(12) United States Patent
Li et al.

(10) Patent No.: US 6,451,030 B2
(45) Date of Patent: Sep. 17, 2002

(54) ROTOR BLADE ANCHOR AND TOOL FOR INSTALLING SAME PARTICULARLLY FOR ARTHROSCOPIC INSTALLATION

(75) Inventors: Lehmann K. Li, Milford; Ernie Corrao, Bethel, both of CT (US)

(73) Assignee: Li Medical Technologies, Inc., Shelton, CT (US)

( * ) Notice: Subject to any disclaimer, the term of this patent is extended or adjusted under 35 U.S.C. 154(b) by 0 days.

(21) Appl. No.: 09/865,143

(22) Filed: May 24, 2001

Related U.S. Application Data

(60) Provisional application No. 60/215,690, filed on Jun. 30, 2000.

(51) Int. Cl.$^7$ .............................................. A61B 17/10
(52) U.S. Cl. ........................... 606/139; 606/232; 606/72
(58) Field of Search ................................ 606/139, 232, 606/72

(56) References Cited

U.S. PATENT DOCUMENTS

| | | | |
|---|---|---|---|
| 2,213,715 A | 9/1940 | Monahan | |
| 4,741,330 A | 5/1988 | Hayhurst | |
| 4,759,765 A | 7/1988 | Van Kampen | |
| 4,776,330 A | 10/1988 | Chapman et al. | |
| 4,823,794 A | 4/1989 | Pierce | |
| 4,898,156 A | 2/1990 | Gatturna et al. | |
| 4,899,743 A * | 2/1990 | Nicholson et al. | 606/139 |
| 5,002,574 A | 3/1991 | May et al. | |
| 5,041,129 A | 8/1991 | Hayhurst et al. | |
| 5,163,946 A | 11/1992 | Li | |
| 5,203,787 A | 4/1993 | Noblitt et al. | |
| 5,217,486 A | 6/1993 | Rice et al. | |
| 5,354,298 A | 10/1994 | Lee et al. | |
| 5,372,604 A | 12/1994 | Trott | |
| 5,405,359 A * | 4/1995 | Pierce | 606/232 |
| 5,443,482 A | 8/1995 | Stone et al. | |
| 5,464,425 A | 11/1995 | Skiba | |
| 5,464,427 A | 11/1995 | Curtis et al. | |
| 5,486,197 A | 1/1996 | Le et al. | |
| 5,531,792 A | 7/1996 | Huene | |
| 5,540,718 A | 7/1996 | Bartlett | |
| 5,545,180 A | 8/1996 | Le et al. | |
| 5,569,303 A | 10/1996 | Johnson | |
| 5,662,681 A | 9/1997 | Nash et al. | |
| 5,941,882 A | 8/1999 | Jammet et al. | |
| 6,068,648 A | 5/2000 | Cole et al. | |
| 6,702,934 | 8/2000 | Li | |
| 6,117,161 A | 9/2000 | Li et al. | |
| 6,174,323 B1 * | 1/2001 | Biggs et al. | 606/144 |
| 6,228,096 B1 * | 5/2001 | Marchand | 606/139 |

FOREIGN PATENT DOCUMENTS

| | | |
|---|---|---|
| EP | 0270704 | 6/1988 |
| FR | 2622430 | 5/1989 |

* cited by examiner

Primary Examiner—Rodney M. Lindsey
(74) Attorney, Agent, or Firm—Ostrolenk, Faber, Gerb & Soffen, LLP

(57) ABSTRACT

A method for securing an anchor to biological tissue, the anchor being detachably and pivotably mounted to an insertion tool, the anchor having a longitudinal axis, the insertion tool having a first axis that extends longitudinally with respect to the insertion tool and a second axis which extends perpendicularly to the first axis, the method including releasably holding the anchor at a distal end of the insertion tool with the anchor being held at least partly within a sheath member of the insertion too.

26 Claims, 2 Drawing Sheets

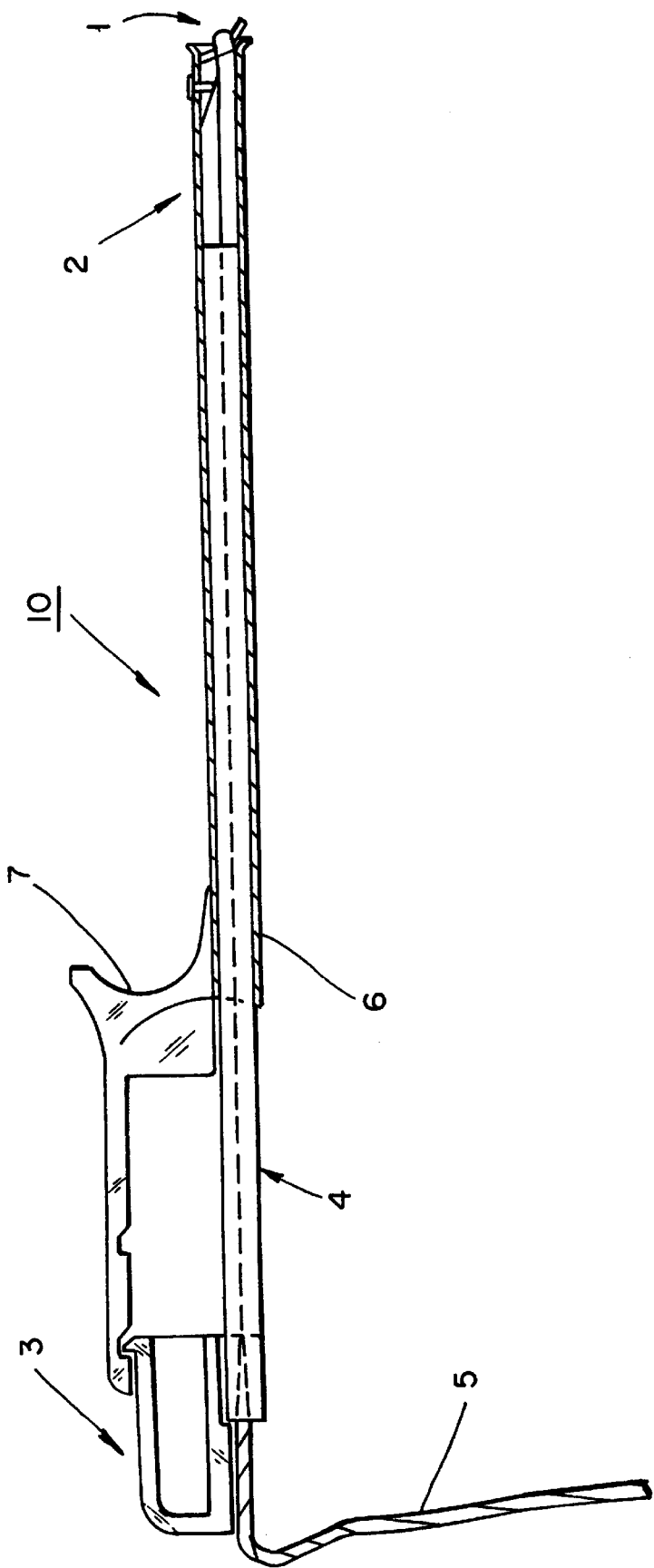

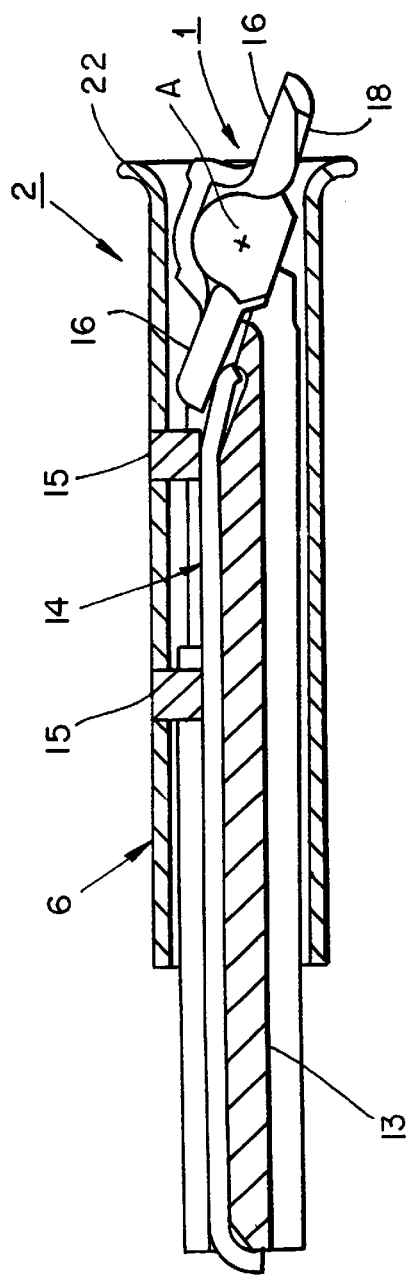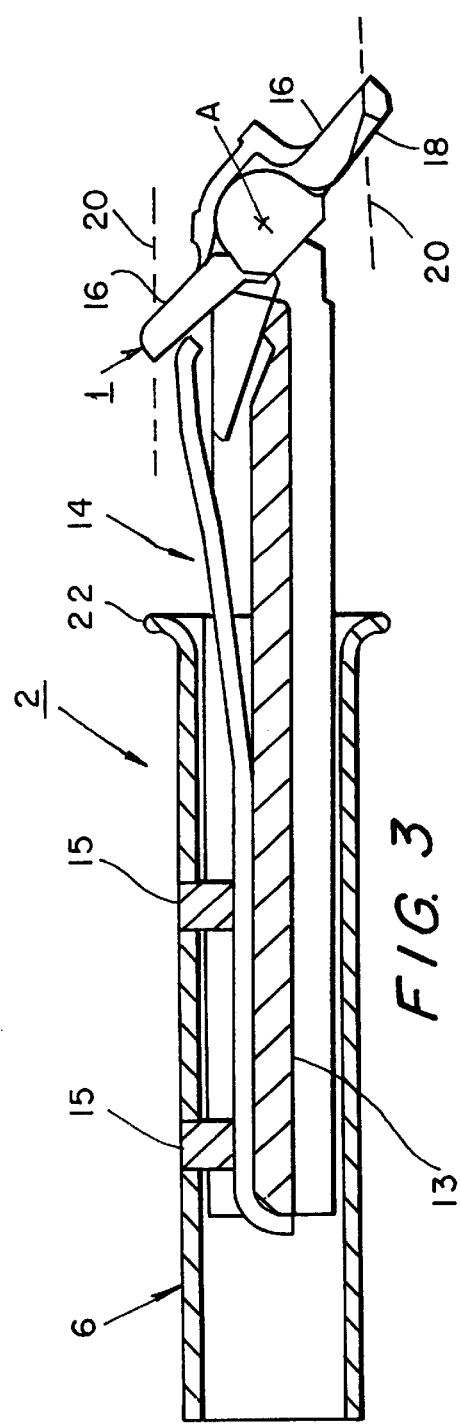

ROTOR BLADE ANCHOR AND TOOL FOR INSTALLING SAME PARTICULARLLY FOR ARTHROSCOPIC INSTALLATION

CROSS-REFERENCE RELATED APPLICATIONS

This application claims priority to U.S. provisional application No. 60/215,690 filed Jun. 30, 2000.

BACKGROUND OF THE INVENTION

The invention relates to fasteners or anchors and, more particularly, to fasteners or anchors for securement into biological tissue, particularly bone. The invention finds particular application in the securement of sutures to bone, such as the attachment of torn ligaments or ligament replacements to the bone through attachment of the suture to the anchor.

In the medical field, it is frequently necessary to securely attach elements such as ligaments (e.g. rotator cuff ligaments, anterior cruciate ligaments) and prosthetics, to a bone. Such attachment requires, initially, that an anchor be secured within the bone itself. Once the anchor is secured, the ligament or prosthetic can be attached to the anchor through, for example, sutures extending from the anchor.

Various techniques exist for securing an anchor within a bone. In U.S. Pat. No. 6,117,161, assigned to Li Medical Technologies, Inc., for example, a longitudinally extending groove is first made in the bone. An anchor, disposed perpendicularly to an insertion handle, is then inserted into the groove and screwed into the bone until the anchor is held securely therein. Since the anchor is disposed perpendicularly to the handle, it is necessary to prepare a groove large enough to accommodate the size of the anchor including its entire length.

Bones are made of a relatively hard outer layer of tissue made of cortical bone cells and a softer inner layer of tissue made of cancellous cells. By making such grooves in the bone, a larger amount of the harder cortical bone cells must be removed thereby decreasing the affixing strength available for securing the anchor within the bone.

In U.S. Pat. No. 6,102,934, also assigned to Li Medical Technologies, Inc., a rotor blade inserter includes a pushing member having a cam surface thereon that engages with an anchor. The pushing member slides in a channel of a shaft. A collar is disposed on and threaded with a stationary gripping member of a handle. When the handle is rotated and the gripping member is held stationary, the channel of the shaft also rotates, imparting this rotation to the pusher member and thus the collar. The threads of the collar then move with respect to the threads of the stationary gripping member, causing the collar to traverse along the handle, transferring the translational motion to the pushing member, which in turn produces a rotational movement of the anchor about an axis perpendicular to the shaft axis through the engagement of the anchor with the cam surface. In order to insert the anchor into a bone, the surgeon must rotate a handle of the device and also hold the stationary gripping member to allow the collar to traverse the handle. This operation can be cumbersome and difficult to effectuate. An embodiment is disclosed where a spring trigger can be used to apply a force upon the pushing channel when the spring trigger is actuated. However, actuation of the trigger is an additional manipulation which must be performed. In many surgical applications, a surgeon's hands are occupied by numerous tasks and so it is important to provide a device which can be actuated with as few movements as possible and/or with one hand.

In co-pending U.S. application Ser. No. 09/580,777 filed May 26, 2000, a rotor blade anchor and tool therefor is described. The tool and anchor comprises a handle having a first axis that extends longitudinally with respect to the handle, and a second axis that extends perpendicularly to the first axis, an anchor pivotably coupled to the handle so that the anchor is pivotable about the second axis and a biasing member disposed on the handle, the biasing member biasing the anchor toward a position which is substantially perpendicular to the first axis, the handle being rotatable about the first axis to allow the anchor to rotate about the first axis, the biasing member causing the anchor to penetrate into a bore hole in the biological tissue by pivoting about the second axis, and to screw into the bore hole to attain a position which is substantially perpendicular to the first axis when the anchor is inserted into the bore hole in the biological tissue.

In U.S. Pat. No. 5,203,787 to Noblitt et al., a hole is drilled in a bone and then an anchoring device is inserted into the hole so that a longitudinal axis of the anchoring device is parallel to a longitudinal axis of the hole. A force is then applied to a suture coupled to the anchoring device thereby causing the anchoring device to rotate within the cancellous cells of the bone so that the anchor extends perpendicularly to the longitudinal axis of the hole. The anchor is then held within the bone by abutting against the inside of the harder cortical bone cells. The technique of Noblitt et al., however, requires complex manipulation of the suture to achieve the desired orientation of the anchor.

See also U.S. Pat. No. 5,569,303 to Johnson for an apparatus and method for attaching an object to bone.

Moreover, modern trends in surgery include the restoration of bodily function and form, or repair of anatomical structures through the use of minimally invasive surgical techniques. The ability to surgically repair damaged tissues or joints creating as few and as small incisions as possible, and with ease of manipulation, produces less trauma to the patient, less pain and generally better clinical outcomes.

Thus, there exists a need in the art for a minimally invasive method and device which more securely attaches an anchor within a bone than devices and techniques of the prior art, which does so using a minimum of operator steps and which can be used arthroscopically, employing minimally invasive surgical techniques.

The present invention is an improvement to the above devices in that the anchor is at least partially concealed and spring loaded such that direct axial insertion and arthroscopic use are possible.

SUMMARY OF THE INVENTION

It is, therefore, an object of the present invention to provide an apparatus and minimally invasive method for delivering an anchor simply and securely into human tissue.

A further object of the invention is to provide an apparatus and method for emplacing an anchor into a borehole in substantial alignment with the borehole and once inserted, activated so that it engages with the walls of the borehole by moving to a position substantially perpendicular to the borehole.

Such an anchor would be suitable, for example, to repair rotator cuff and other ligament injuries such that the appropriate attachment strength is provided.

It is a further object of the invention to provide such an apparatus which is suitable for arthroscope use in body tissue.

The present invention is directed to an apparatus and a method for delivering an anchor member which sets in biological tissue. The method for delivering the anchor member into biological tissue comprises the following basic steps:

(a) accessing and preparing the intended insertion site;
(b) inserting into the site, through a cannula or otherwise, an anchor member that is set through applying a rotational motion;
(c) after insertion into the site, the anchor member engages the tissue by moving from a first position substantially aligned with a borehole at the site to a substantially perpendicular position (to the insertion angle) through a rotational force. Steps (a) through (c) may be performed through open or minimally invasive surgical techniques, i.e., arthroscopic techniques.

According to a further aspect, the invention comprises a method for securing an anchor to biological tissue, said anchor being detachably and pivotably mounted to an insertion tool, said anchor having a longitudinal axis, said insertion tool having a first axis that extends longitudinally with respect to said insertion tool and a second axis which extends perpendicularly to said first axis, said method comprising the steps of: releasably holding said anchor at a distal end of said insertion tool with said anchor being held at least partly within a sheath member of the insertion tool; inserting said anchor held by said insertion tool, with said longitudinal axis of said anchor being disposed in an orientation that is not perpendicular to said first axis, into a borehole in said biological tissue; actuating a member at a proximal end of said insertion tool thereby to move said anchor distally out of said sheath; applying a biasing force to the anchor to bias said anchor toward a position that is substantially perpendicular to said first axis; said biasing force causing said anchor to rotate about the second axis and engage with a sidewall of said bore hole and to penetrate into said sidewall; rotating said tool about said first axis, whereby said anchor is screwed into said object as said insertion tool is rotated about said first axis and simultaneously rotated about said second axis until said anchor achieves an orientation substantially perpendicular to said first axis; when the anchor is secured in said sidewall, releasing the anchor from said insertion tool, leaving the anchor secured in the biological tissue; and withdrawing the insertion tool.

The above and other objects are also achieved by a tool for securing an anchor to biological tissue, said tool comprising: a handle, a hollow sheath member coupled to the handle having a first axis that extends longitudinally with respect to said handle, and a second axis that extends perpendicularly to said first axis; the distal end of said sheath member being adapted to pivotably and releasably hold an anchor so that said anchor is pivotable about said second axis and being adapted to hold the anchor at least partly surrounded by said sheath member in a first position; a biasing member adapted to bias said anchor about said second axis toward a position which is substantially perpendicular to said first axis; a pusher member adapted to apply a force to said anchor to cause said anchor to move from said first position to a second position distally out of said sheath member; said handle being rotatable about said first axis to allow said anchor, once in said second position out of the sheath member, to rotate about said first axis, said biasing member causing said anchor to penetrate into a bore hole in said biological tissue by pivoting about said second axis, thereby to screw into said bore hole to attain a position which is substantially perpendicular to said first axis when said anchor is inserted into said bore hole in said biological tissue.

These aspects, as well as others, will become apparent upon reading the following disclosure and corresponding drawings.

BRIEF DESCRIPTION OF THE DRAWINGS

For the purpose of illustrating the invention, there is shown in the drawings a form which is presently preferred, it being understood, however, that the invention is not limited to the precise arrangements and instrumentalities shown in the drawings:

FIG. 1 is cut away side view of an anchor insertion tool and anchor in accordance with the invention;

FIG. 2 is an enlarged cut away side view of a distal end of the tool and anchor of FIG. 1; and FIG. 3 is a cut away side view of the tool and anchor of FIG. 2 shown in the extended position.

DETAILED DESCRIPTION OF THE INVENTION

In FIG. 1, one preferred embodiment of an insertion tool and anchor assembly is shown. The anchor 1 is attached to the distal end 2 of an optionally disposable insertion tool 10. The tool 10 need not be disposable and may be reusable. A movable handle element or trigger 3 is connected to a pusher element 4, which in turn is releasably connected to the anchor 1. The pusher element 4 is housed in a sheath member or hollow shaft 6. A finger grip 7 is provided for the surgeon's finger. The handle 3 is compressed toward grip 7 to trigger actuation of the anchor 1. The anchor 1 is threaded with suture 5 which is housed in a slot in the shaft 6. In this embodiment, the anchor 1 is ready to be deployed by inserting the generally axially aligned anchor 1 into a pre-drilled bone hole. As shown, the anchor need only be "generally" aligned with the shaft 6. In fact, it can be disposed at an acute angle to the shaft 6, so long as it is substantially within the inner diameter of the shaft 6 upon insertion into the tissue. As shown, the anchor is partly contained within the hollow shaft 6 prior to securement in tissue.

In FIGS. 2 and 3, a close up side view of the anchor 1 and the distal end 2 of the insertion tool are shown. FIG. 2 shows the anchor 1, as it may be positioned within the distal end 2 of the insertion tool, prior to insertion into a pre-drilled bone hole. The anchor 1 is at least partially contained within the distal end 2 of the insertion tool and is removably connected to a pusher element 13. The trailing end of the anchor 1 is situated between the inside wall of the sheath member 6 and the distal end of a spring lever 14. The distal end of the spring lever 14 is biased outwardly, but is restricted by elements 15. FIG. 3 shows the anchor 1 during the deployment process (prior to the application of a rotational force but while in a pre-drilled bone hole), having been completely exposed from the distal end 2 of the insertion tool. By moving the pusher element 13 far enough distally to expose the trailing end of the anchor 1 and the leading end of the spring lever 14 (by moving handle 3 toward finger grip 7), the anchor 1 is positioned away from a near axial alignment to a more perpendicular position. The proximal end of the spring lever or leaf spring 14 is maintained under load by the restricting elements 15 so the distal end of the spring lever 14 can exert sufficient force on the trailing end of the anchor 1 to begin deployment. Once the anchor tips 16 are forced against the inside walls of a pre-drilled bone hole (shown by phantom lines 20), the application of a rotational force to the tool will initiate the deployment process. The anchor has cutting edges 18 disposed on opposite sides thereof, as also shown, for example in U.S. Pat. No. 6,102,934, for cutting into the borehole walls, as the tool, and thus anchor, are rotated. The rotation causes the anchor to screw into the borehole. The spring lever 14 imparts a biasing force to the anchor 1, causing the anchor initially to engage the wall of the borehole when the spring expands by moving outside the shaft 6, due to sliding motion of the member 4 acting on pusher element 13.

In use, the surgeon inserts the anchor into the borehole in the biological tissue, e.g. bone. The member 3 is compressed toward grip 7, causing the anchor 1 to move distally out of the sheath. The spring 14 biases the anchor, causing it to pivot about axis A into an engagement with the boreholes. By rotating the tool 10, the anchor is screwed into the borehole. Once the anchor is secured, the tool is withdrawn, leaving the anchor, and any attached sutures, secured in the borehole. The anchor is preferably not fixed to the distal end 6 of the tool, so the tool will release the anchor when it is withdrawn proximally. Alternatively, the anchor may be held by the tool using a frangible or releasable (quick disconnect) connection, as will be appreciated by those of skill in the art.

The anchor may be shaped as a circular disc, oval, kidney, pointed, polygonal, have any symmetrical or asymmetrical geometrical configuration, or comprise a solid or have fenestrations. Also, the anchor may be two dimensional, or three dimensional. The anchor can be attached to a washer, button, or any flexible element.

Additionally, the anchor may be made from metal, polymer, bioabsorbable material, bone, or any other biocompatible material or combination thereof.

To insert the anchor, a hole in the bone may or may not need to be predrilled, depending on the sharpness of the leading point of the anchor, or whether there may be cutting surfaces (such as threads) on the anchor or the insertion tool.

The insertion tool may be designed as a single use, disposable or a reusable instrument. Also, the insertion tool may be designed for open or minimally invasive surgery. The activation element to initiate the outward bias of the anchor, shown as spring lever 14 in the described embodiment, may be a spring of another type, lever, rod, or any other suitable design element. Near the distal tip of the insertion tool may be a shoulder stop 22 to indicate the maximum depth of anchor insertion into biologic tissue for more precise and reliable engagement of the anchor in tissue.

An advantage of the invention is that, since at least a portion of the anchor is contained within the distal end of the insertion tool, the anchor is better suited for arthroscopic usage. The anchor will be protected such that it can be passed through such obstructions as a flap in a cannula, or multiple layers of soft tissue.

Another advantage is that only a small insertion opening (in the form of a predrilled bone hole) is required to implant the anchor, thus minimizing the trauma to the biological tissue and enhancing the fixation capability of the anchor.

Yet another advantage of the anchor and insertion tool assembly is the simplicity and convenience of a single use device. Additionally, the rotation of a pitched cutting edge (Rotor Blade Anchor) design allows the surgeon to have tactile feedback of the anchor engagement into the bone hole, just as one would have while emplacing a screw anchor into bone.

The sheath 6 as well as pusher element 4 can be rigid or may have some degree of flexibility to allow bending thereof as required, for example, for arthroscopic use.

While preferred embodiments of the invention have been disclosed, various modes of carrying out the principles disclosed herein are contemplated as being within the scope of the following claims. Therefore, it is understood that the scope of the invention is not to be limited except as otherwise set forth in the claims.

What is claimed is:

1. A method for securing an anchor to biological tissue, said anchor being detachably and pivotably mounted to an insertion tool, said anchor having a longitudinal axis, said insertion tool having a first axis that extends longitudinally with respect to said insertion tool and a second axis which extends perpendicularly to said first axis, said method comprising the steps of:

releasably holding said anchor at a distal end of said insertion tool with said anchor being held at least partly within a sheath member of the insertion tool;

inserting said anchor held by said insertion tool, with said longitudinal axis of said anchor being disposed in an orientation that is not perpendicular to said first axis, into a borehole in said biological tissue;

actuating a member at a proximal end of said insertion tool thereby to move said anchor distally out of said sheath member;

applying a biasing force to the anchor to bias said anchor toward a position that is substantially perpendicular to said first axis;

said biasing force causing said anchor to rotate about the second axis and engage with a sidewall of said bore hole and to penetrate into said sidewall;

rotating said tool about said first axis, whereby said anchor is screwed into said biological tissue as said insertion tool is rotated about said first axis and simultaneously rotated about said second axis until said anchor achieves an orientation substantially perpendicular to said first axis;

when the anchor is secured in said sidewall, releasing the anchor from said insertion tool, leaving the anchor secured in the biological tissue; and withdrawing the insertion tool.

2. The method as claimed in claim 1, wherein in said inserting step, said longitudinal axis of said anchor is more closely parallel to said first axis.

3. The method as claimed in claim 1, wherein in said inserting step, the biasing force is prevented from exerting a force on the anchor.

4. The method as claimed in claim 1, wherein said step of applying a biasing force to cause rotation of said anchor about said second axis comprises activating a biasing member disposed in said insertion tool to cause said anchor to rotate about the second axis.

5. The method as claimed in claim 1, wherein said biological tissue has an outer layer and an inner layer, said outer layer having a strength that is greater than a strength of said inner layer, and wherein said step of inserting includes inserting said anchor into said inner layer.

6. The method as claimed in claim 1, wherein said biological tissue is bone.

7. The method as claimed in claim 5, wherein:

said biological tissue is bone;

said outer layer is cortical tissue of said bone; and said inner layer is cancellous tissue of said bone.

8. The method as claimed in claim 1, wherein said anchor includes at least one cutting edge disposed thereon to penetrate into said sidewall.

9. The method as claimed in claim 1, further comprising holding at least a portion of said anchor at the distal end of said insertion tool in a first position in the sheath member of the insertion tool such that the anchor is more closely aligned with a longitudinal axis of the sheath member, applying a pushing force to the anchor whereby the anchor slides with respect to the sheath member into a second position whereby the anchor is not protected by the sheath member, and causing a biasing member to exert the biasing force on the anchor when the anchor is in the second position thereby causing the anchor to rotate about the second axis.

10. The method as claimed in claim 9, wherein the step of applying the pushing force comprises applying the pushing force to a holder element for the anchor.

11. The method as claimed in claim 10, wherein the step of applying the pushing force causes the biasing member to apply the biasing force to the anchor.

12. The method as claimed in claim 9, wherein said step of inserting further includes holding said biasing member in a compressed state in said sheath member so that an outer periphery of said anchor in said first position is smaller than an outer periphery of said anchor when said sheath member does not compress said biasing member when said anchor is in said second position.

13. A tool for securing an anchor to biological tissue, said tool comprising:
a handle, a hollow sheath member coupled to the handle having a first axis that extends longitudinally with respect to said handle, and a second axis that extends perpendicularly to said first axis;
the distal end of said sheath member being adapted to pivotably and releasably hold an anchor so that said anchor is pivotable about said second axis, and being adapted to hold the anchor being at least partly surrounded by said sheath member in a first position;
a biasing member adapted to bias said anchor about said second axis toward a position which is substantially perpendicular to said first axis;
a pusher member adapted to apply a force to said anchor to cause said anchor to move from said first position to a second position distally out of said sheath member;
said handle being rotatable about said first axis to allow said anchor, once in said second position out of the sheath member, to rotate about said first axis, said biasing member causing said anchor to penetrate into a bore hole in said biological tissue by pivoting about said second axis, thereby to screw into said bore hole to attain a position which is substantially perpendicular to said first axis when said anchor is inserted into said bore hole in said biological tissue.

14. The tool as claimed in claim 13, wherein said sheath member further comprises a shoulder protrusion extending outwardly from said sheath member to limit a depth of insertion of said anchor into said bore hole.

15. The tool as claimed in claim 13, further comprising said anchor and wherein said anchor further comprises a hub at a center thereof, said hub including an opening for attachment of sutures therein.

16. The tool as claimed in claim 13, further comprising said anchor and wherein:
said anchor further includes a leading side and a trailing side, said leading and trailing sides being disposed so that when said anchor is inserted into said biological tissue, said leading side is inserted into said biological tissue before said trailing side; and
at least one of said leading side and said trailing side includes a cutting portion thereon.

17. The tool as claimed in claim 16, wherein both of said leading side and said trailing side of said anchor include said cutting portion.

18. The tool as claimed in claim 16, wherein said biasing member is a spring.

19. The tool as claimed in claim 18, wherein the spring comprises a leaf spring.

20. The tool as claimed in claim 16, wherein said biasing member is in contact with said anchor and said sheath member and is initially held in a compressed state by said sheath member in said first position of the anchor and moves to an extended state when the anchor moves out of said sheath member to said second position.

21. The tool as claimed in claim 20, wherein, upon insertion of said anchor into said biological tissue, said anchor compresses said biasing member due to engagement of said anchor with said bore hole.

22. The tool as claimed in claim 21, wherein said anchor compresses said biasing member so that an outer periphery of the combination of said anchor and said biasing member is smaller than an outer periphery of said combination when said anchor does not compress said biasing member.

23. The tool as claimed in claim 13, further comprising a suture coupled to said anchor.

24. The tool as claimed in claim 13, further wherein the biasing member is a leaf spring having an extendible portion; and
further comprising a cam member holding the extendible portion of the leaf spring in a compressed state when the anchor is in the sheath member and when the anchor is pushed out of the sheath member, said extendible portion of the leaf spring is allowed to extend to an uncompressed state because said cam member no longer acts on the extendible portion.

25. The tool as claimed in claim 13, further comprising the anchor.

26. The tool as claimed in claim 13, wherein the sheath member and pusher member are flexible.

* * * * *